(12) United States Patent
Konecke

(10) Patent No.: US 7,244,392 B1
(45) Date of Patent: Jul. 17, 2007

(54) SLIDE-IN CASSETTE FOR A CUP FOR TESTING OF DRUGS OF ABUSE

(75) Inventor: Jeffery A. Konecke, Mebane, NC (US)

(73) Assignee: Inverness Medical Switzerland GmbH, Zug (CH)

( * ) Notice: Subject to any disclaimer, the term of this patent is extended or adjusted under 35 U.S.C. 154(b) by 0 days.

(21) Appl. No.: 09/575,429

(22) Filed: May 22, 2000

(51) Int. Cl.
*G01N 33/48* (2006.01)
(52) U.S. Cl. .................. 422/58; 422/56; 422/61; 422/101; 422/102; 436/164; 436/166; 436/169; 436/808; 436/810
(58) Field of Classification Search ............ 422/56–58, 422/61, 102–104; 436/164, 166, 169, 808, 436/810
See application file for complete search history.

(56) References Cited

U.S. PATENT DOCUMENTS

| | | | |
|---|---|---|---|
| 3,552,213 A | 1/1971 | Auchapt et al. | |
| 4,084,937 A | 4/1978 | Beach | 23/259 |
| 4,797,256 A | 1/1989 | Watlington, IV | |
| 4,827,944 A | 5/1989 | Nugent | |
| 4,976,923 A | 12/1990 | Lipsky et al. | |
| 5,022,411 A | 6/1991 | Guirguis | |
| 5,119,830 A * | 6/1992 | Davis | 422/102 |
| 5,215,102 A | 6/1993 | Guirguis | |
| 5,352,410 A | 10/1994 | Hansen et al. | |
| 5,403,551 A | 4/1995 | Galloway et al. | |
| 5,429,804 A | 7/1995 | Sayles | |
| 5,501,837 A | 3/1996 | Sayles | |
| 5,569,225 A | 10/1996 | Fleury | |
| 5,595,187 A | 1/1997 | Davis | |
| 5,603,903 A | 2/1997 | Copelan | |
| 5,656,502 A | 8/1997 | MacKay et al. | |
| 5,739,041 A | 4/1998 | Nazareth et al. | 436/518 |
| D404,812 S * | 1/1999 | Chipkowski | D24/107 |
| 5,882,600 A | 3/1999 | Davis | |
| 5,897,840 A | 4/1999 | Owens, Jr. et al. | |
| 5,916,815 A * | 6/1999 | Lappe | 422/56 |
| 5,976,895 A | 11/1999 | Cipkowski | 436/518 |
| 6,054,099 A | 4/2000 | Levy | |
| 6,063,341 A | 5/2000 | Fassbind et al. | |

(Continued)

FOREIGN PATENT DOCUMENTS

GB   1 218 746   12/1967

(Continued)

*Primary Examiner*—Lyle A. Alexander
(74) *Attorney, Agent, or Firm*—Fitch, Even, Tabin & Flannery

(57) ABSTRACT

A specimen cup (100) has slide-in cassette (102) hermetically sealed in a chamber (104), with a outer partition being transparent. The cassette comprised chemical test strips (106) used to provide testing of drugs of abuse or other chemical or biological substances. The cassette is designed to draw urine up from the front bottom of the cup, thereby reduces the amount of urine required to perform the test. Further the cassette is designed to form isolated test channels through the use of strategically placed vertical and horizontal bars which are hermetically sealed. The cup further comprises a spill prevention flap or float (108) and an optionally enlarged sample collection portion (110) for its operation. The windows of the test cassette are covered with transparent fluid-resistant plate to prevent urine from accidentally spill onto the strips.

20 Claims, 2 Drawing Sheets

U.S. PATENT DOCUMENTS

| | | |
|---|---|---|
| 6,074,606 A | 6/2000 | Sayles |
| 6,277,646 B1 | 8/2001 | Guirguis et al. |
| 6,342,183 B1 * | 1/2002 | Lappe et al. .................. 422/58 |
| 6,576,193 B1 * | 6/2003 | Cui et al. ..................... 422/58 |

FOREIGN PATENT DOCUMENTS

| | | | |
|---|---|---|---|
| GB | 2 031 583 | | 8/1979 |
| WO | 97/33519 | * | 9/1997 |

* cited by examiner

SLIDE-IN CASSETTE FOR A CUP FOR TESTING OF DRUGS OF ABUSE

FIELD OF THE INVENTION

This invention relates to the art of handling, testing, and transporting fluid specimens. More particularly, it relates to a cup with a slide-in cassette to provide testing of drugs of abuse in bodily fluids, such as urine, blood, saliva, etc.

BACKGROUND OF THE INVENTION

Fluid specimens, particularly urine, are normally collected in containers, vials or cups. When it is desired to run tests on liquid or fluid specimens contained in the cups, the lids are normally removed and specimen samples are taken out of the cups and transferred to a test apparatus. In the Instacheck® Drug Screen Drug Test, a urine sample from a cup is drawn up in a pipette and 3-4 drops (~0.2 ml) are then dispensed onto the sample well. The urine then travels up a chemical strip for 3-8 minutes. The chemical strip was pre-coated with drug conjugate on the test band. A colored anti-drug monoclonal antibody colloidal gold conjugate pad is placed at one end of the strip. In the absence of the drug in the urine, the colored antibody colloidal gold conjugate moves along the sample solution upward on the strip chromoatographically by the capillary action to the immobilized drug conjugate zone on the test band region and attaches to the drug conjugate to form a visible line on the antibody complexes with the drug conjugate. Therefore, the formation of a visible precipitate in the test zone occurs when the test urine is negative for the drug. When drug is present in the urine, the drug/metabolite antigen competes with drug conjugate on the test band region for the limited antibody sites on the antibody-colloidal gold conjugate. When a sufficient concentration of drug is present, it will fill the limited antibody binding sites. This will prevent attachment of the colored antibody-colloidal gold conjugate to the drug conjugate zone on the test band region. Therefore, absence of the color band on the test region indicates a positive result.

A difficulty with the Instacheck® test is that the urine needs to be transferred from a cup onto test strips with the lid of the cup removed, thus exposing the operator and work area to possible contamination.

Additionally, the specimen sample could become contaminated as well as the worker and the surrounding equipment. Furthermore, with lid removed, spillage and loss of the unique specimens may occur. Thus, it is the object of this invention to provide a custom designed integrated system composed of a custom collection cup used as a collection and testing vessel and a custom designed slide-in test cartridge to test for drugs of abuse and other chemical and biological substance in urine and other liquid mediums in a closed, safe and secure environment.

DESCRIPTION OF THE PRIOR ART

U.S. Pat. No. 5,119,830 to Davis describes a specimen cup having a valve to selectively operated from outside the specimen cup to introduce fluid specimen for detection of drugs of abuse by chemical strips.

U.S. Pat. No. 5,916,815 to Lappe describes a specimen cup to detect drugs of abuse using intentional false positive to initially preserve anonymity.

U.S. Pat. No. Des. 404,812 describes a multiple drug test card to be housed in a cup for detection of drugs of abuse. It requires sliding a card through a slotted lid and thus exposure, spillage and contamination are possible. The card is neither sealed nor contained within the device and thus can contaminate specimen. Additionally, the card draws sample from the side and required both a maximum and minimum fill requirement which makes exposure and spillage a greater problem as user tries to fill container "just right". If the minimum and maximum fill marks are not followed the test will not function. Too little urine and the test does not run, too much and the test sample is contaminated. The card must be removed at the completion of the test cycle, resulting in exposure and contamination to user and work area. If the sample is positive, the cover is removed and a closed cover is placed on bottle. Again, exposure and spillage is a problem. Lastly again, the card is inserted in the middle of a low bottle resulting in difficulty in reading result and often requiring the user to lift the card out to view or tip bottle to view. Either way exposure and spillage is a problem.

All of the above patents had to use very complicated and/or expensive collection/reagent system. They are troublesome to get quick and easy test results. Additionally, some result in difficulty in transporting or storing the fluid specimen.

SUMMARY OF THE INVENTION

Accordingly, it is an object of the present invention to provide a easy to use, inexpensive, integrated testing system comprised of a collection cup/testing vessel and a slide-in testing cassette housing the chemical/immunological test strips for the testing of drugs of abuse and other chemical and biological substances in urine and other liquid specimens/samples. The integrated system is composed of the custom test cup used to collect the sample and then the same cup is used as the testing vessel and ultimately as the storage and transport container. The test cup also can comprise a spill-prevention and over-fill prevention flap or float. This component is a movable device that is in a vertical position at the start of filling. As urine or other liquid sample is placed in the cup the "flap" will raise to a horizontal position. When raised it cuts off the available space in the cup and creates an artificially filled environment preventing additional liquid from being added to the cup. The cup is designed with a "flat" face, set back in the circular cup to move the viewing area closer to the test device while maintaining a circular type cup at the top and bottom for stability and ease of use. The "flat" viewing window also results in a ergonomically designed cup that is easier to handle when the subject is providing the urine or other sample. The inside bottom of the cup is designed with a sloped bottom (1-3 degrees) to allow for the urine sample or other liquid sample to be channeled towards the test cassette, thus allowing for testing when small volumes of specimen are given. The test cassette is uniquely designed to draw urine from the bottom, thus minimizing the amount of urine needed to perform the test. This design also eliminates the need for minimum sample volume requirements or having to tilt, turn or invert the container to allow sample to contact the test strips. The card is hermetically sealed both around the entire perimeter as well as vertically between each test strips and horizontally below the test regions. This assures that each test strip is isolated within a unique test column and prevents any cross-contamination between the chemicals/substances contained within each test strip. The area of the card where the test regions of the test strips are viewed is covered with a clear material hermetically sealed to the face of the test card to prevent any direct contamination of the test strips from the sample or tampering with the test strips by the operator or donor. There is a sample "pooling" area at the bottom of the test cassette to allow urine or other liquid sample to migrate up to contact the test strips. This "pooling" area functions as an internal sample well. This allows the test strips to be completely enclosed in the device and eliminates any contact from the operator or donor which could cause contamination. Additionally, running horizontally above the "pooling" area is a "dam" designed to restrict the vertical flow of sample up the test strips and contain the sample in the "pooling" area.

BRIEF DESCRIPTION OF THE DRAWINGS

The novel features which are believed to be characteristic of the invention are set forth with particularity in the appended claims. The invention itself, however, both as to its organization and method of operation, may best be understood by reference to the following description, when taken in connection with the accompanying drawing in which:

DETAILED DESCRIPTION OF THE PREFERRED EMBODIMENT

Figure 1:
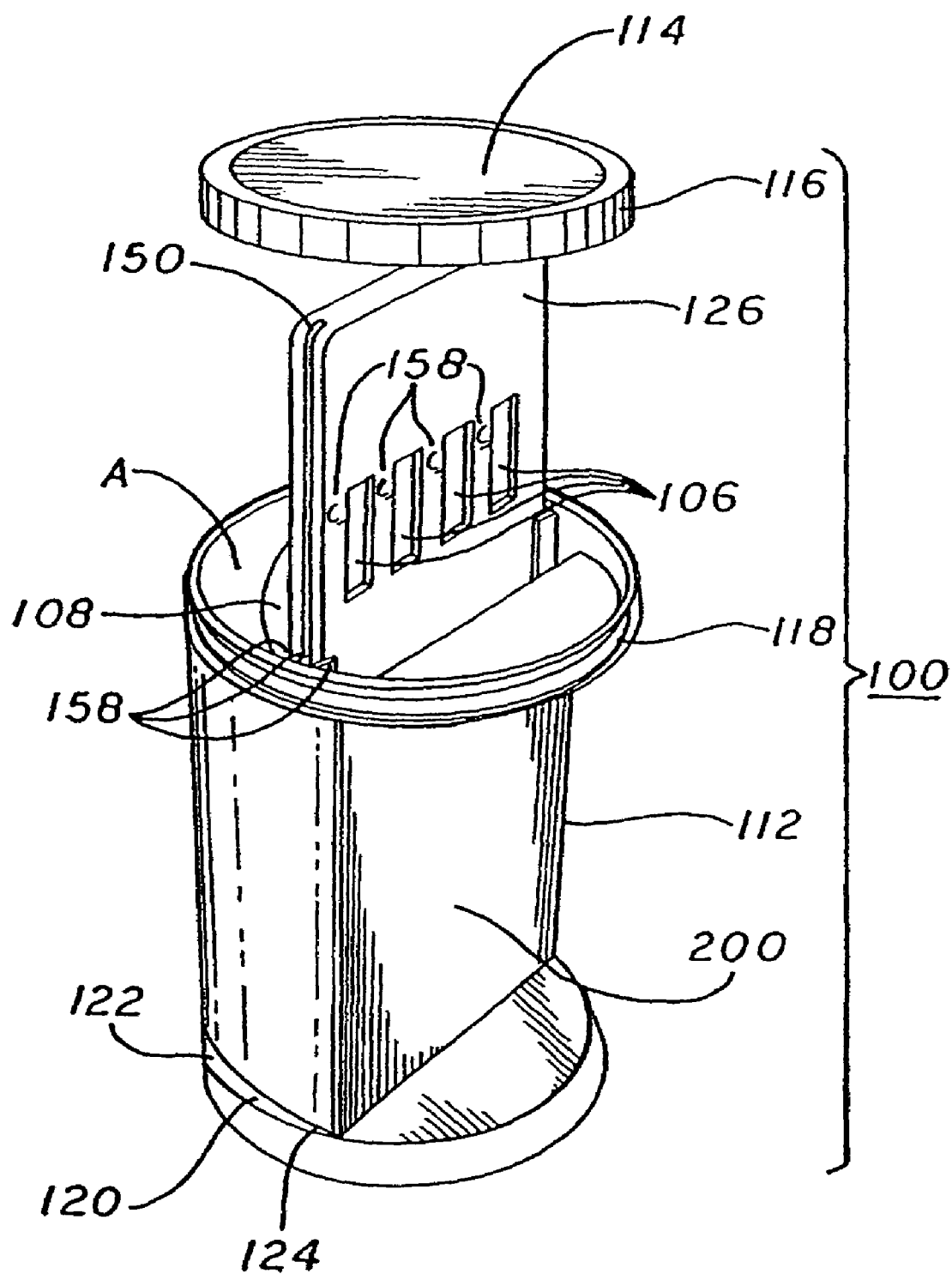
FIG. 1 is a prospective view of the cup for testing drugs of abuse and other chemical and biological substance of the present invention.
Figure 2:
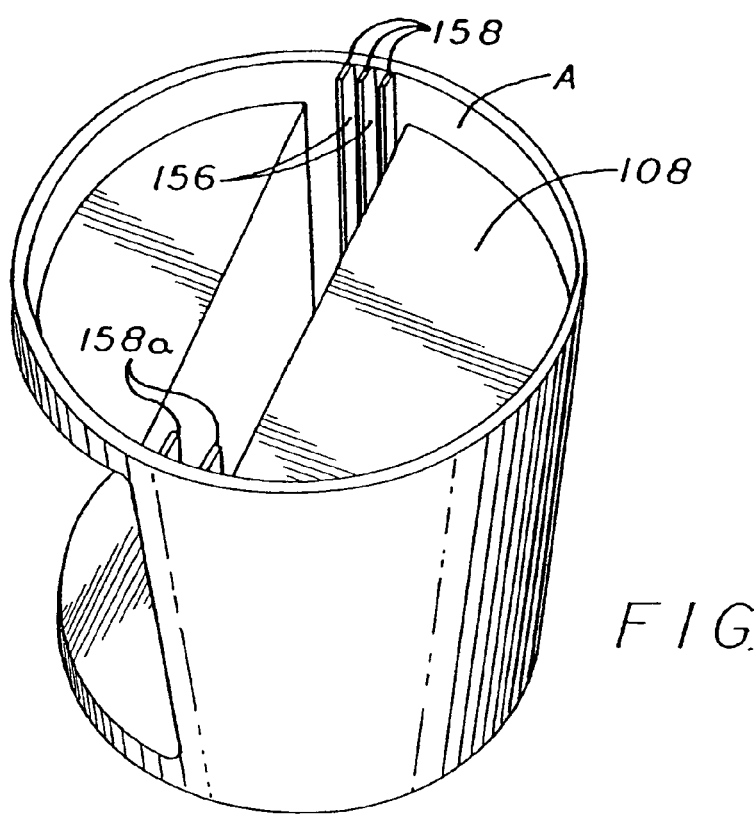
FIG. 2 is a top prospective view of the specimen cup (with the top cover removed) of FIG. 1.

A specimen cup (100) of the present invention includes a base container (112) and a lid (114). The specimen cup (100) is for collecting, testing, storing and transporting a urine specimen and other liquid within a container thereof. The base container (112) can optionally has an expanded sample collection portion to allow more urine to be collected. The lid (114) has threads (116) which mesh with threads (118) of the base container (112) to sealingly hold the lid (114) on the base container 112. In region A behind the chamber (104) to which the cassette (102) is hermetically sealed, there is a urine spill prevention flap or float (108) (see FIG. 2) to which the urine once entered into the sample collection portion will be prevented from splashing during transport or storage. The flap or float is free to travel vertically in region A under the pressure from the fluid specimen, such as urine.

The base container (112) and its lid (114) are constructed of a material which is transparent, and impervious to fluid specimens contained therein. The materials include but not limited to thermoplastics, specialty plastics, thermosets, engineering plastics.

Thermoplastics include but not limited to: polyamideimide (PAI), polyethersulfone (PES), polyarylsulfone (PAS), polyetherimide (PEI), polyarylate (PAR), polysulfone (PSO), polyamide (PA), polycarbonate (PC), styrene-maleic anhydride (SMA), chlorinated PVC (CPVC), poly(methylmethacrylate) (PMMA), styrene-acrylonitrile (SAN), polystyrene (PS), acrylonitrile-butadiene-styrene (PS), acrylonitrile-butadiene-styrene (ABS), poly(ethyleneterephthalate) (PET), poly(vinylchloride) (PVC), polyetherketone (PEK), polyetheretherketone (PEEK), polytetrafluoroethylene (PTFE), poly(phenylene sulfide) (PPS), liquid crystal polymer (CCP), nylon-6,6, nylon-6, nylon-6,12, nylon-11, nylon 12, acetal resin, low and high density polypropylene (PP), high density polyethylene (HDPE), low density polyethylene (LDPE), polystyrene, ethylene-vinyl acetate, poly-vinyl-acetate, polyacrylic, etc., or a copolymer or a combination thereof.

Specialty plastics include but not limited to fluorocarbon polymers and infusible film products such as Kapton, Upilex polyimide film etc., a copolymer or a combination thereof. Thermosets include but not limited to phenolics, epoxies, urea-formaldehyde, silicones, etc., a copolymer or a combination thereof. Engineering plastics include but not limited to acetyl resins, polyamide, polyetherimides, polyesters, liquid crystal polymers, polycarbonate resins, poly(phenylene ether) alloys, polysulfone resins, polyamideimide resins, etc., a copolymer or a combination thereof.

Figure 3:
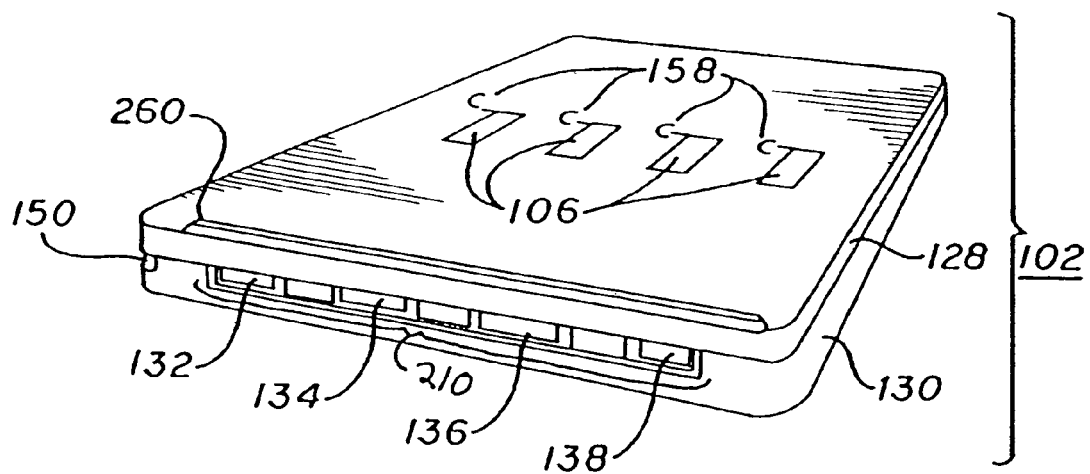
FIG. 3 is a (bottom) prospective view of the slide-in cassette.

The bottom floor (120) of the cup can be optionally sloped from the backside (122) downwardly at 1-3° towards the front side (124). This forces the fluid (by gravity) to moves forward, hence reduces the fluid specimen needed for the testing for drugs of abuse by the cassette. The front of the cup has a retracted flat face (200) designed to move the viewing area closer to the test cassette. The base and top of the cup remain circular to allow for use of standard covers and provide a stable base. Inside the cup are custom channels (156) used to guide and oriented the cassette in the device. The cassette is inserted into the cup (100) with its outside edges (150) anchored between the bars (158). The slot on the left side of the cassette will only align with the triple channel on the left side of the cup. The bars (158) ensure the cassette is inserted facing the correct way for viewing and ensure proper placement within the container. Because one of the fluids that may be tested is urine, as the urine cools in a closed environment condensation may occur. The tracks are designed to orient the cassette for viewing while allowing movement of air between the cassette and face of cup to prevent condensation forming on inside of cup. The chemical test strips (106) of various, flexible configurations such as 11-nor-Δ-9-tetra hydrocannabinol-9 carboxylic acid (THC), Cocaine (COC), Methamphetamine/amphetamine (MAP), 1-(1'-phenylcyclohexyl) piperidine (PCP), Morphine (MOR) etc. are housed in a custom cassette (126). The cassette has four distinct, isolated test channels (132, 134, 136 and 138) which house the test strips. Each test channel has a clear, sealed window for viewing the results. Each channel is hermetically sealed both vertically and horizontally to ensure four unique test areas and prevent any direct or cross contamination. As seen in FIG. 3 the cassette is formed by an upper (128) and lower (130) member. Near the bottom of the cassette is a horizontally running "dam" (260) that when the upper and lower members are hermetically sealed together creates a sample "pooling" area (210). This "pooling" area (210) allows sample to contact the test strips while eliminating the need for the test strips (106) to be exposed. Thus the entire test strip is contained within the cassette eliminating potential contamination, adulteration or tampering. When the test card is inserted into the test container, the sample "pools" around the base of the test strips and wicks vertically up the strips. As the sample moves up the strip, the result is observed through the clear viewing windows. The clear viewing windows prevent direct contact with the test regions of the test strips either by the operator, donor or specimen.

During operation, a specimen, such as urine, is provided in the custom collection/test cup (100). The test cassette (126) is inserted into the test cup through custom bars (156) and the lid of the cup (114) is put in place. The urine specimen then enters the "pooling" areas (210) at the base of the test cassette and begins to wick up the test strips. When the urine contacts the test strips, the characteristics thereof, in conjunction with chemicals in the test strips causes the test strips to change color, thereby providing a visual indication to an operator in accordance with the precalibrated indicator marking beside the respective test strips corresponding to such characteristics. The changes in color are then easily observed and read by the operator through the transparent window on the test card and the face of the collection/test cup.

After testing is completed, the specimen can be stored, transported or disposed of in the collection/test cup used for this testing process. This eliminates having to remove the test device, change lids, transfer specimen or otherwise handle the urine sample in any way that could result in exposure or contamination to the operator, donor of surrounding environment.

It will be appreciated by those of ordinary skill in the art that the specimen cup of this invention allows collection, testing, transportation and storage of a fluid specimen, such as urine, with chemical strips of characteristics of the specimen without exposing it to the outside atmosphere, or having to come into direct contact with the specimen himself, thereby eliminating the possibility of contaminating him/her-self or surrounding equipment with the fluid specimen contained in the specimen cup, or possibly spilling and losing the entire unique specimen itself.

I claim:

1. A specimen cup for testing fluid specimen, when fluid specimen is contained therein, said cup comprising:
   a container used to collect the fluid specimen and made of transparent material, said container having a circular top opening and a circular bottom being of uniform circular cross section except for a recessed flat front wall which is intermediate to said top and bottom;
   said container having means integrated with the interior surface thereof which provide a receptacle inside of said container and adjacent the interior surface of said front wall which receptacle is designed to slidably receive a cassette,
   a cassette having a substantially flat front surface, which cassette is slidably received within said receptacle that is integrated within said container and that is located near said flat front wall, said cassette containing at least one test strip, configured to provide an indication of a characteristic of the specimen regarding a drug of abuse, when said at least one test strip is exposed to the drug of abuse, and having a window in said flat front surface aligned with said strip, said receptacle only slidably receiving said cassette with said window facing said flat front wall of said container so said test strip can be easily viewed through said window and through said transparent flat front wall while said cassette is disposed within the container; and
   a lid configured to cover said top opening with the cassette inside, wherein said receptacle extends vertically below said lid.

2. A specimen cup for testing fluid specimen contained therein, said cup comprising a container used to collect a fluid specimen and made of transparent material, which container has a uniform circular cross section except for a recessed flat front face, said container having a circular top opening and a circular bottom being of uniform circular cross section except for a recessed flat front wall which is intermediate to said top and bottom, further comprising means integrated with the interior surface thereof which provide a receptacle inside of said container and adjacent the interior surface of said front wall which receptacle is designed to slidably receive a cassette, a container lid, and a sealed cassette which is received within said receptacle that is integrated within said container, said cassette having a substantially flat front surface and containing chemical strips means to provide an indication of a characteristic of said specimen regarding drugs of abuse, wherein said receptacle locates said cassette within said container with said flat front surface near said recessed flat front face so that a viewing area is provided close to said cassette front surface so said test strip can be easily viewed through said window and through said transparent flat front wall while said cassette is disposed within the container.

3. A specimen cup as in claim 2, wherein said cassette has a window in said front flat surface in association with said chemical strips and is slidably inserted into said receptacle, which receptacle has different opposite channels that mate with only one of said cassette's outside edges and orient said cassette for proper testing and viewing with said window facing said flat front face of said container.

4. A specimen cup as in claim 2, wherein said chemical strips comprise test strips used to test for THC, COC, MAP, PCP and MOR.

5. A specimen cup as in claim 2, further comprising a hinged flap adjacent to a rim of said container, the hinged portion of the flap being affixed to an interior surface of said container in a position which partially blocks the opening of said container, said flap being configured to reduce the splashing of said fluid specimen during collection, testing, transport and storage.

6. A specimen cup as in claim 2, further comprising a floating member configured to substantially fill a volume directly above said fluid specimen once said fluid specimen is entered into said cup, said floating member being configured to reduce the splashing of said fluid specimen during collection, testing, transport and storage.

7. A specimen cup as in claim 2, further comprising a dam structure attached to said cassette and located so as to form a recessed pooling area in said cassette when said fluid specimen flows into said cassette's open bottom end portion to form said pooling area, said pooling area being configured to expose said chemical strips to the fluid specimen, while recessing the exposed portion of said chemical strips sufficiently within said cassette to minimize potential contamination of said chemical strips.

8. A specimen cup as in claim 2, wherein said lid is constructed to mate with a rim of said container and provide a substantially sealed closure.

9. A specimen cup as in claim 8, wherein said lid is independent of said container.

10. A specimen cup as in claim 2, wherein said cup is constructed of a material selected from the group consisting of thermoplastics, specialty plastics, thermosets, and engineering plastics.

11. A specimen cup as in claim 10, wherein said thermoplastics is selected from the group consisting of polyamideimide (PA1), polyethersulfone (PES), polyarylsulfone (PAS), polyetherimide (PEI), polyarylate (PAR), polysulfone (PSO), polyamide (PA), polycarbonate (PC), styrene-maleic anhydride (SMA), chlorinated PVC (CPVC), poly (methylmethyacrylate) (PMMA), styrene-acrylonitrile (SAN), polystyrene (PS), acrylonitrile-butadiene-styrene (ABS), poly(ethyleneterephthalate) (PET), poly(vinylchloride) (PVC), polyetherketone (PEK), polyetheretherketone (PEEK), polytetrafluoroethylene (PTFE), poly(phenylene sulfide) (PPS), liquid crystal polymer (CCP), nylon-6,6, nylon-6, nylon-6,12 nylon-11, nylon 12, acetal resin, low and high density polypropylene (PP), high density polyethylene (HDPE), low density polyethylene (LDPE), polystyrene, ethylene-vinyl acetate, poly-vinyl-acetate and polyacrylic.

12. A specimen cup as in claim 2, wherein said cassette comprises a plurality of isolated test channels which each house one of said chemical strips for testing for one drug of abuse.

13. A specimen cup as in claim 12, wherein each of said isolated test channels has a clear, sealed window associated therewith in said flat front surface for viewing the results of a test.

14. A specimen cup as in claim 13, wherein said clear, sealed window is formed by a transparent fluid-resistant sheet laying on top of said strip to prevent fluid specimen from accidentally spilling and contaminating said strip.

15. A specimen cup for testing a fluid specimen contained therein, said cup comprising a container used to collect a fluid specimen, said container having a circular top opening and a circular bottom being of uniform circular cross section except for a recessed flat front wall which is intermediate to said top and bottom, a container lid, a cassette having a sealed window in a substantially flat front surface thereof, which cassette is removably and slidably receivable in said receptacle in said container, which receptacle is designed to slidably receive said cassette, said cassette containing chemical test strips to provide an indication of a characteristic of said specimen regarding drugs of abuse, and a dam structure attached to said cassette and located so as to form a recessed pooling area in said cassette when said fluid specimen flows into said cassette's open bottom end portion to form said pooling area, said pooling area being configured to expose said cassette's interior test strips to the fluid specimen, while recessing the exposed portion of said test strips sufficiently within said cassette to minimize potential contamination of the test strips, said receptacle being located near said flat front wall and said container being made of transparent material so that said chemical test strips can be easily viewed through said window and through said transparent flat front wall while said cassette is disposed within the container.

16. A specimen cup as in claim 15, wherein a bottom floor of said container slopes downwardly at 1-3° towards the bottom of said receptacle, said floor being configured to allow said specimen to be channeled towards said cassette.

17. A specimen cup for testing a fluid specimen contained therein, which cup comprises:
   a container used to collect a fluid specimen, which container is made of transparent material, having a circular top opening and a circular bottom being of uniform circular cross section except for a recessed flat front wall which is intermediate to said top and bottom, and has a receptacle integrated with the interior surface of said container and located inside said container and near said flat front wall which receptacle is designed to slidably receive a cassette,
   a cassette proportioned for slidable insertion into said receptacle, which cassette contains at least one test strip that is created to provide an indication of the presence of a chemical component, for which said specimen is being tested, when said test strip is exposed to the component with said cassette being disposed within said receptacle within said container,
   said cassette having a window in a substantially flat front surface which window is aligned with said test strip and side edge regions of said cassette and said receptacle being constructed to only receive said cassette with said window facing said flat front wall so said test strip can be easily viewed through said window and through said transparent flat front wall while said cassette is disposed within the container; and
   a lid configured to close said top opening with said cassette disposed within said receptacle inside the container.

18. The specimen cup of claim 17 wherein said window is sealed against liquid entry.

19. The specimen cup of claim 17 wherein said receptacle which slidably receives said cassette has bars and said cassette has different channels formed along its opposite side edges which mate with said bars in said receptacle in only one orientation so that said window faces said flat front wall.

20. The specimen cup of claim 17 wherein a bottom floor of said container slopes downwardly at 1-3° towards the bottom of said cassette when inserted in said receptacle allowing said specimen to be channeled toward the lower end of said cassette.

* * * * *